(12) United States Patent
Casasanta, III

(10) Patent No.: US 9,376,614 B2
(45) Date of Patent: Jun. 28, 2016

(54) OPTICALLY ACTIVE EPOXY

(75) Inventor: Vincenzo Casasanta, III, Woodinville, WA (US)

(73) Assignee: Empire Technology Development LLC, Wilmington, DE (US)

( * ) Notice: Subject to any disclaimer, the term of this patent is extended or adjusted under 35 U.S.C. 154(b) by 542 days.

(21) Appl. No.: 13/878,531

(22) PCT Filed: Aug. 22, 2012

(86) PCT No.: PCT/US2012/051835
§ 371 (c)(1),
(2), (4) Date: Apr. 9, 2013

(87) PCT Pub. No.: WO2014/031111
PCT Pub. Date: Feb. 27, 2014

(65) Prior Publication Data
US 2014/0203190 A1 Jul. 24, 2014

(51) Int. Cl.
*C08G 59/14* (2006.01)
*C09K 11/06* (2006.01)
*C08G 59/06* (2006.01)
*C08G 59/62* (2006.01)
*G01N 21/64* (2006.01)

(52) U.S. Cl.
CPC .............. *C09K 11/06* (2013.01); *C08G 59/066* (2013.01); *C08G 59/621* (2013.01); *G01N 21/64* (2013.01)

(58) Field of Classification Search
None
See application file for complete search history.

(56) References Cited

U.S. PATENT DOCUMENTS

| 4,983,672 | A | * | 1/1991 | Almer | C08G 59/066 525/122 |
| 5,451,446 | A | * | 9/1995 | Kincaid | B24D 3/28 428/143 |
| 6,103,446 | A | | 8/2000 | Devlin et al. | |
| 8,227,561 | B1 | * | 7/2012 | Carlson | C08G 18/758 526/319 |
| 2007/0128379 | A1 | | 6/2007 | Hirai | |
| 2011/0240918 | A1 | | 10/2011 | Ootsuki et al. | |
| 2012/0041102 | A1 | * | 2/2012 | Chun | C08G 59/1438 523/456 |

FOREIGN PATENT DOCUMENTS

| JP | 5-43656 A | * | 2/1993 | |
| JP | 5-178960 A | * | 7/1993 | |
| JP | WO 03104295 A1 | * | 12/2003 | ............. C08L 63/00 |

OTHER PUBLICATIONS

HCAPLUS 2003:991558 for WO 2003/104295 A1, Nakahara et al., Dec. 18, 2003, five pages.*
International Search Report and Written Opinion for PCT/US2012/051835dated Feb. 15, 2013.
Wegner et al., Oligiondenopyrenes: A New Class of Polycyclic Aromatics, *J. Org. Chem.* (Oct. 21, 2006), 71(24):9080-9087 (Abstract).

* cited by examiner

*Primary Examiner* — Robert Sellers
(74) *Attorney, Agent, or Firm* — Pepper Hamilton LLP

(57) ABSTRACT

An optically active composition is described. The composition may include a copolymer of two or more polyepoxides covalently linked by a fused arene.

25 Claims, 3 Drawing Sheets

OPTICALLY ACTIVE EPOXY

CLAIM OF PRIORITY

This application is a U.S. national stage filing under 35 U.S.C. §371 of International Application No. PCT/US2012/051835 filed Aug. 22, 2012 and entitled "Optically Active Epoxy", which is incorporated herein by reference in its entirety.

BACKGROUND

Millions of articles of manufacture constantly change hands during, for example, processing of raw materials, transportation, manufacturing, disposal of waste, and so forth. Identification and tracking of these articles of manufacture is a significant challenge. Because, identification and tracking of waste articles, more particularly hazardous and electronic waste, is mandated by law in many countries, effective methods for identifying waste articles are needed.

SUMMARY OF INVENTION

Some embodiments include compounds having a general structure

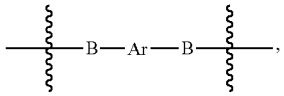

where B is a polyepoxide and Ar is a fused arene. In some embodiments, the compound may further include a crosslinker having functional groups such as, for example, epoxy, phenol, hydroxyl, amine, carboxylate, isocyanate, or any combination thereof, and in particular embodiments, the compound may exhibit fluorescence when excited by ultraviolet light.

Further embodiments are directed to compositions including a copolymer of two or more polyepoxides covalently linked by a fused arene. In some embodiments, the copolymer may be of a general formula

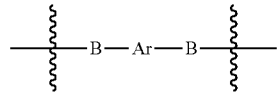

where B is a polyepoxide and Ar is a fused arene. In certain embodiments, the copolymer may be crosslinked by a crosslinker having functional groups such as, for example, epoxy, phenolic, hydroxyl, amine, carboxylate, isocyanate, or any combination thereof, and in other embodiments, the composition may further include one or more additives such as, for example, fibers, surfactants, organic binders, polymeric binders, crosslinking agents, coupling agents, aramid fibres, lubricants, mold release agents, pentaerythritol tetrastearate, nucleating agents, anti-static agents, conductive blacks, carbon fibers, carbon nanotubes, organic antistatic agents, polyalkylene ethers, alkylsulfonates, polyamide-containing polymers, catalysts, colorants, inks, dyes, antioxidants, stabilizers, plasticizers, impact agents, flame retardants, or combinations thereof.

Other embodiments are directed to articles of manufacture including a copolymer of two or more polyepoxides covalently linked by a fused arene. In some embodiments, the copolymer may have a general formula

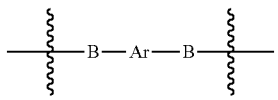

where B is a polyepoxide and Ar is a fused arene. In certain embodiments, the copolymer may be crosslinked by a crosslinker having functional groups such as, for example, epoxy, phenolic, hydroxyl, amine, carboxylate, isocyanate, or any combination thereof. In other embodiments, the article of manufacture may further include one or more additives such as, for example, fibers, surfactants, organic binders, polymeric binders, crosslinking agents, coupling agents, aramid fibres, lubricants, mold release agents, pentaerythritol tetrastearate, nucleating agents, anti-static agents, conductive blacks, carbon fibers, carbon nanotubes, organic antistatic agents, polyalkylene ethers, alkylsulfonates, polyamide-containing polymers, catalysts, colorants, inks, dyes, antioxidants, stabilizers, plasticizers, impact agents, flame retardants, or combinations thereof.

Yet other embodiments are directed to methods for preparing an optically active epoxy. In some embodiments, such methods may include providing at least one functionalized fused arene and contacting the functionalized fused arene with a polyepoxide under conditions that allow the functionalized fused arene to react with the polyepoxide to produce an optically active epoxy. In some examples, such methods may further include contacting the optically active epoxy with one or more crosslinking agents, one or more curing agents, or combinations thereof under conditions that allow the one or more crosslinking agent, one or more curing agents, or combinations thereof to become incorporated into the optically active epoxy. In certain embodiments, the methods may further include molding, forming a film, cutting, exposing to heat, UV light, or combinations thereof, blending, compounding, extruding, or combinations thereof.

Still further embodiments are directed to methods for preparing an optically active epoxy laminant. Such methods may include providing one or more functionalized fused arene, contacting the one or more functionalized fused arene with a polyepoxide under conditions that allow the one or more functionalized fused arene to react with the polyepoxide to produce an optically active epoxy, contacting the optically active epoxy with a crosslinking agent, curing agent, or combinations thereof, to form an optically active epoxy prepreg mixture, applying the optically active prepreg mixture to a mat or cloth to form a prepreg, and heating the prepreg to produce an epoxy laminant. In some embodiments, such methods may further include contacting the optically active epoxy with one or more additional components, one or more additives, or combinations thereof under conditions that allow the one or more additional components, one or more additives, or combinations thereof to become incorporated into the optically active epoxy. In certain embodiments, the methods of the invention may further include contacting a first epoxy laminant with one or more second epoxy laminants under conditions that allow the first epoxy laminant and the second epoxy laminant to fuse.

Still other embodiments are directed to methods for identifying a component of a device. In some embodiments, such methods may include providing a device having a component including a copolymer of two or more polyepoxides covalently linked by fused arene, irradiating the device with ultraviolet light, and identifying the component based on its fluorescence. In certain embodiments, the fluorescence may involve emission of visible light. Examples of identifying may include, but are not limited to, determining a type of the component, determining materials associated with the component, identifying warnings regarding the component, identifying the component manufacturer, determining the manufacture or expiration dated, and the like.

Further embodiments are directed to functionalized fused arenes having the general formula X—Ar—X', where Ar is a fused arene having 10 to 100 carbon atoms, X may include a phenol, aniline, or benzoic acid, and X' may include a phenol, aniline or benzoic acid. In particular embodiments, X and X' are substituted at opposite ends of the fused arene.

BRIEF DESCRIPTION OF FIGURES

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

Figure 1:
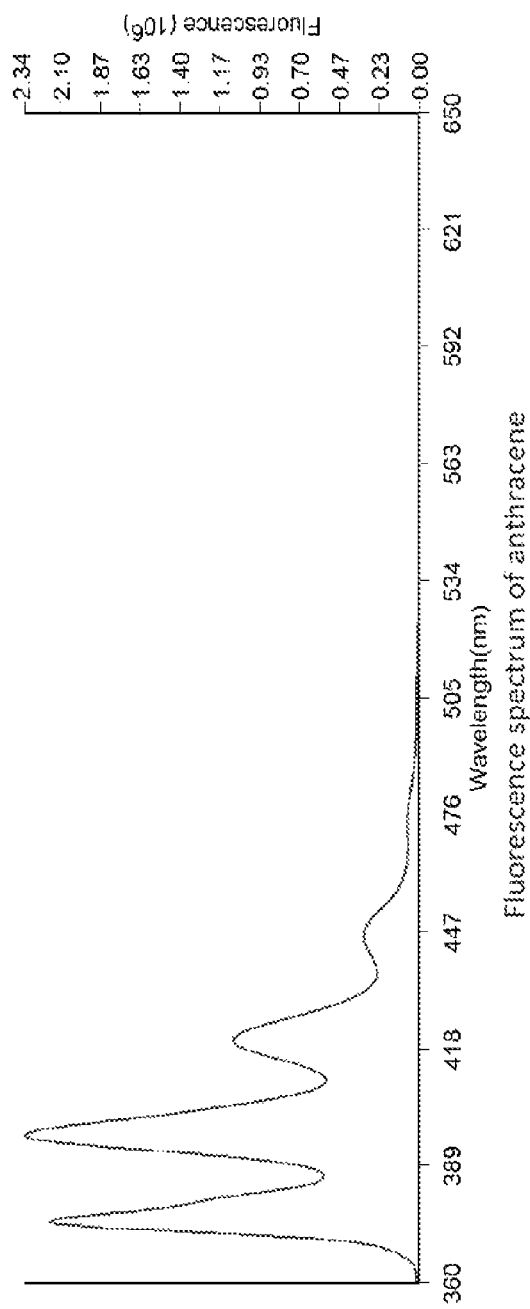
FIG. 1 depicts the fluorescence spectrum of anthracene.

Embodiments are directed to compounds and crosslinking agents that exhibit optical activity, and polymer compositions including these compounds or crosslinking agents. For some compounds and crosslinking agents, the optical activity exhibited may include fluorescence. Thus, such compounds and crosslinking agents can be used for marking or otherwise identifying articles of manufacture or other components that that are made from polymer compositions that incorporate these compounds or crosslinking agents. For example, in some embodiments, information associated with the article of manufacture such as, for example, manufacturer, composition, manufacture date, expiration date, part number, serial number, warnings regarding the article, and the like can be determined based on the optical activity exhibited by the article. Certain embodiments are directed to methods for identifying articles of manufacture or components of various devices or articles of manufacture using the optically active compounds or compositions. Other embodiments are directed to methods of making optically active compounds and compositions, and methods for making articles of manufacture such compounds and compositions.

As described herein, "optical activity" refers to fluorescence and "optically active" compounds refer to compounds that exhibit fluorescence. The compounds of various embodiments may include copolymers of one or more polyepoxide covalently linked by fused arenes. For example, certain such copolymers may be of general formula I:

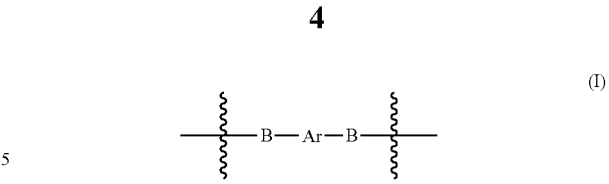

where B is a polyepoxide and Ar is a fused arene. In such embodiments, B can be any polyepoxide including, for example, bisphenol-A type epoxy, bisphenol-F type epoxy, naphthalene-type epoxy, diphenylfluorene-type epoxy, triglycidyl aminophenol epoxy, triglycidyl aminocresol epoxy, tetraglycidyl diaminodiphenylmethane epoxy, tetraglyidyl m-xylylene amine epoxy, N,N-diaminocresol epoxy, phenol novolac-type epoxy, cresol novolac-type epoxy, biphenyl-type epoxy, dicyclopentadiene-type epoxy, or combinations thereof. Ar can be any fused arene. For example, illustrative fused arenes include, but are not limited to, acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, chrysene, dibenz(a,h)anthracene, fluoranthene, fluorene, indeno(1,2,3-cd)pyrene, perylene, phenanthrene, pyrene, or combinations thereof. In some embodiments, such copolymers may further include units derived from an epoxy functional crosslinker, a phenolic functional crosslinker, a hydroxyl functional crosslinker, an amine functional crosslinker, a carboxylate functional crosslinker, an isocyanate functional crosslinker, or combinations thereof. As such, copolymers of embodiments of the invention can have numerous configurations and compositions.

In some embodiments, the fused arene may include a compound of formula (II):

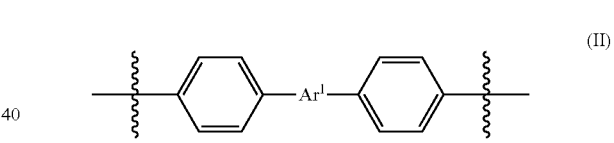

where, $Ar^1$ is a fused arene having 10 to 100 carbon atoms such as, for example, acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, chrysene, dibenz(a,h)anthracene, fluoranthene, fluorene, indeno(1,2,3-cd)pyrene, perylene, phenanthrene, pyrene, or combinations thereof.

In some instances, compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The formulas are shown without a definitive stereochemistry at certain positions. The present invention includes all stereoisomers of such formulas and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general formula may be obtained by stereospecific synthesis using optically pure starting materials or reagents of known configuration.

Optical properties of various embodiments of the compound may vary. In some embodiments, the compound may be fluorescent in visible region of the electromagnetic spectrum. For example, the compound may have emission wavelength of about 300 nm, about 320 nm, about 340 nm, about 360 nm, about 380 nm, about 400 nm, about 420 nm, about 440 nm, about 460 nm, about 480 nm, about 500 nm, about 520 nm, about 540 nm, about 560 nm, about 580 nm, about 600 nm, about 620 nm, about 640 nm, about 660 nm, about 680 nm, about 700 nm, or any value or range between any two of these values. In some embodiments, the excitation wavelength of the compound may be about 10 nm, about 50 nm, about 100 nm, about 150 nm, about 200 nm, about 250 nm, about 300 nm, about 350 nm, about 400 nm, or any value or range between any two of these values.

In some embodiments, the copolymers described above may be combined with one or more additional components to provide a polymer composition. For example, in various embodiments, compositions including the copolymers of the invention may include fillers, fibers, surfactants, organic binders, polymeric binders, crosslinking agents, coupling agents, aramid fibres, lubricants, mold release agents, pentaerythritol tetrastearate, nucleating agents, anti-static agents, conductive blacks, carbon fibers, carbon nanotubes, organic antistatic agents, polyalkylene ethers, alkylsulfonates, polyamide-containing polymers, catalysts, colorants, inks, dyes, antioxidants, stabilizers, plasticizers, impact agents, flame retardants, or combinations thereof. In certain embodiments, such compositions may include fibers such as, for example, silicon carbide (SiC) fibers, glass fibers, or carbon fibers, and in particular embodiments, such fibers may be incorporated into a mat or a cloth.

The various additional components of such embodiments can be provided for any reason and may enhance or provide any property of the copolymer. For example, in certain embodiments, one or more additional components may be included in a composition to provide improved structural characteristics such as strength, integrity, shape, and combinations thereof of the copolymer containing composition. In other embodiments, additional components may be incorporated into polymer compositions of the invention to provide characteristics such as, for example, improved hardness, plasticity, thermoplasticity, flowability, electrical and/or thermal conductivity, thermal stability, malleability, color, chemical inertness, biodegradability, or combinations thereof.

Further embodiments are directed to articles of manufacture including a copolymer of one or more polyepoxide covalently linked by a fused arene such as those described above. In certain embodiments, the copolymer in the article of manufacture may include a compound of formula (I):

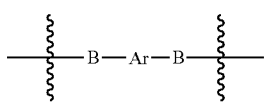

(I)

where B is a polyepoxide and Ar is a fused arene. As above, in various embodiments, B can be any polyepoxide including, for example, bisphenol-A type epoxy, bisphenol-F type epoxy, naphthalene-type epoxy, diphenylfluorene-type epoxy, triglycidyl aminophenol epoxy, triglycidyl aminocresol epoxy, tetraglycidyl diaminodiphenylmethane epoxy, tetraglyidyl m-xylylene amine epoxy, N,N-diaminocresol epoxy, phenol novolac-type epoxy, cresol novolac-type epoxy, biphenyl-type epoxy, dicyclopentadiene-type epoxy, or combinations thereof. Similarly, Ar can be any fused arene known in the art including, for example, acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, chrysene, dibenz(a,h)anthracene, fluoranthene, fluorene, indeno(1,2,3-cd)pyrene, perylene, phenanthrene, pyrene, or combinations thereof. In certain embodiments, the fused arene Ar may be of general formula (II):

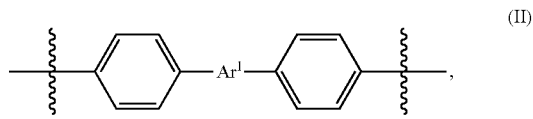

(II)

where $Ar^1$ may be any fused arene having 10 to 100 carbon atoms. For example, $Ar^1$ may be acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, chrysene, dibenz(a,h)anthracene, fluoranthene, fluorene, indeno(1,2,3-cd)pyrene, perylene, phenanthrene, pyrene, or combinations thereof.

In particular embodiments, the copolymers in the article of manufacture may be crosslinked by one or more crosslinking agents or one or more curing agents. Any crosslinking agents or curing agents known in the art may be used for this purpose. For example, in certain embodiments, crosslinking agents or curing agents may be one or more of an epoxy functional crosslinker, a phenolic functional crosslinker, a hydroxyl functional crosslinker, an amine functional crosslinker, a carboxylate functional crosslinker, an isocyanate functional crosslinker, or combinations thereof. In some embodiments, the copolymers used in the preparation of article of manufacture may include one or more additional components, one or more additives, or combinations thereof. Any additives or additional components known in the art may be added to the copolymer to provide, modify or improve any properties exhibited by the copolymer and necessary for article of manufacture such as, for example, hardness, strength, integrity, shape, plasticity, thermoplasticity, flowability, electrical and/or thermal conductivity, thermal stability, malleability, color, chemical inertness, biodegradability, or combinations thereof. For example, the additives may include fillers, fibers, surfactants, organic binders, polymeric binders, crosslinking agents, coupling agents, aramid fibres, lubricants, mold release agents, pentaerythritol tetrastearate, nucleating agents, anti-static agents, conductive blacks, carbon fibers, carbon nanotubes, organic antistatic agents, polyalkylene ethers, alkylsulfonates, polyamide-containing polymers, catalysts, colorants, inks, dyes, antioxidants, stabilizers, plasticizers, impact agents, flame retardants, or combinations thereof. In certain embodiments, fibers such as, SiC fibers, glass fibers, or carbon fibers may be added to the article of manufacture, and in some embodiments, such fibers may be incorporated into a mat or a cloth.

Article of manufacture can be any type of article known in the art such as, for example free-standing films, prepregs, fibers, foams, molded articles, woven articles, non-woven articles, fiber reinforced composites, and the like. In some exemplary embodiments, the article of manufacture or the copolymers and compositions described herein can be incorporated into support parts, electrical components, electrical connectors, electrical housings, electrical covers, electrical insulators, printed wiring laminated boards, housings, covers, brackets, support structures, enclosures, solid sheets, co-extruded sheets, multi-walled sheets, or subcomponents and components in consumer products.

The articles of manufacture incorporating the copolymers and compositions described herein will, generally, exhibit the same optical activity as the copolymers themselves. Therefore, in certain embodiments, the article of manufacture may be fluorescent, and in particular embodiments, the article of manufacture may have an emission wavelength of about 300 nm, about 320 nm, about 340 nm, about 360 nm, about 380 nm, about 400 nm, about 420 nm, about 440 nm, about 460 nm, about 480 nm, about 500 nm, about 520 nm, about 540 nm, about 560 nm, about 580 nm, about 600 nm, about 620 nm, about 640 nm, about 660 nm, about 680 nm, about 700 nm, or any value or range between any two of these values when excited at an excitation wavelength of, for example, 10 nm, about 50 nm, about 100 nm, about 150 nm, about 200 nm, about 250 nm, about 300 nm, about 350 nm, about 400 nm, or any value or range between any two of these values. In some embodiments, the fluorescence of the article of manufacture created by the copolymer or composition may act as a fluorescent tag for the article of manufacture allowing the article of manufacture to be identified or certain information about the article of manufacture can be identified by the fluorescence.

The compounds and materials described herein may be prepared using any methods known in the art. Thus, some embodiments are directed to methods for preparing an optically active epoxy. In some embodiments, the method may include providing at least one functionalized fused arene and contacting the functionalized fused arene with a polyepoxide under conditions that allow the functionalized fused arene to react with the polyepoxide to produce an optically active epoxy. Any conditions known in the art may be used for allowing the one or more functionalized fused arene to react with the polyepoxide. For example, in some embodiments, such conditions may include heating, reducing pressure, purging, mixing, blending, extruding, compounding, reacting, exposing to heat or UV light, and the like or combinations thereof. In certain embodiments, the reaction conditions may include, but are not limited to, elevated temperatures, reduced temperatures, increased pressure, anhydrous conditions, or combinations thereof. In certain embodiments, it may be desirable to maintain the conditions for a particular amount of time.

In certain embodiments, contacting the polyepoxide with the fused arene may include, for example, a Friedel Crafts reaction. In some embodiments, such methods may include the step of adding a catalyst to the reaction mixture to facilitate the reaction. Any catalyst suitable for the particular coupling reaction may be used in such embodiments. For example, in certain embodiments, the catalyst may be a metal halide catalyst such as, for example, aluminum chloride, ferric chloride, cuprous chloride, and the like, or combinations thereof, and in particular embodiments, the catalyst may be, for example, N-bromosuccinimide, samarium (III) triflate, acetonitrile, sulphuric acid, and the like or combinations thereof.

In certain embodiments, the method may further include contacting an optically active epoxy with one or more crosslinking agents, one or more curing agents, or combinations thereof under conditions that allow the one or more crosslinking agent, one or more curing agents, or combinations thereof to become incorporated into the optically active epoxy. Any crosslinking agents or curing agents known in the art may be used. Examples of crosslinking agents or curing agents include, but are not limited to, an epoxy functional crosslinker, a phenolic functional crosslinker, a hydroxyl functional crosslinker, an amine functional crosslinker, a carboxylate functional crosslinker, an isocyanate functional crosslinker, or combinations thereof. In certain embodiments, contacting the optically active epoxy with the crosslinking agents or curing agents may be achieved by mixing of the components using for example, a blender or extruder, and in some embodiments, parameters such as rate of mixing, temperature, pressure, humidity, and the like may be controlled depending on the means for mixing used and the particular components mixed and their properties.

In some embodiments, the method may include contacting the optically active epoxy with one or more additional components, one or more additional additives, or combinations thereof, under conditions that allow the one or more additional components, one or more additives, or combinations thereof, to become incorporated into the optically active epoxy. In various embodiments, the additional components and additives that can be incorporated into the optically active epoxy can include, but are not limited to, fillers, fibers, surfactants, organic binders, polymeric binders, crosslinking agents, coupling agents, aramid fibres, lubricants, mold release agents, pentaerythritol tetrastearate, nucleating agents, anti-static agents, conductive blacks, carbon fibers, carbon nanotubes, organic antistatic agents, polyalkylene ethers, alkylsulfonates, polyamide-containing polymers, catalysts, colorants, inks, dyes, antioxidants, stabilizers, plasticizers, impact agents, flame retardants, and the like or combinations thereof. In some embodiments, the one or more additional components may be fibers such as, for example, SiC fibers, glass fibers, carbon fibers or combinations thereof. In certain embodiments, the method may include contacting a mat or a cloth with the optically active epoxy, and the mat or cloth of such embodiments may include fibers such as, for example, SiC fibers, glass fibers, carbon fibers, and the like or combinations thereof. Particular additives may be desirable for particular applications because of certain properties unique to a particular additive. Factors such as, for example, particular application, cost, scalability, and the like may be used to guide the choice of additives.

The methods of various embodiments may further include other processing steps such as, for example, molding, forming a film, cutting, heating, irradiating with UV light, or combinations thereof, blending, compounding, extruding, and the like or combinations thereof.

Certain embodiments are directed to a method for preparing an optically active epoxy laminant. In such embodiments, the method may include providing one or more functionalized fused arene, contacting the one or more functionalized fused arene with a polyepoxide under conditions that allow the one or more functionalized fused arene to react with the polyepoxide to produce an optically active epoxy, and applying the optically active epoxy to a fiber containing mat or cloth to form a prepreg. The method may further include heating prepreg or irradiating the prepreg with, for example, UV light to produce an epoxy laminant. Any conditions known in the art may be used for reacting the one or more functionalized fused arene with the polyepoxide, and reacting may include, for example, a Friedel Crafts reaction. In some embodiments, conditions for forming the optically active epoxy may include, for example, heating, reducing pressure, purging, mixing, blending, extruding, compounding, reacting, irradiating with UV light, and the like or combinations thereof.

In some embodiments, such methods further include contacting the optically active epoxy with a crosslinking agent, curing agent, or combinations thereof and/or any additional components or additives before applying the optically active epoxy to the mat or cloth, thereby producing a pre-impregnation mixture that includes the optically active epoxy and any such components. In certain embodiments, the optically active epoxy, which may or may not include crosslinking agents, curing agents, additional components or additives, may be in a liquid form. Thus, in some embodiments, the pre-impregnation mixture may further include a solvent. Such solvents may be removed during heating or irradiating of the prepreg or after this step using known methods. In some embodiments, the mat or cloth may include fibers such as, for example, SiC fibers, glass fibers, carbon fibers, and the like or combinations thereof. Crosslinking agents or curing agents useful in the methods presented above include, but are not limited to, phenolic functional crosslinkers, hydroxyl functional crosslinkers, amine functional crosslinkers, carboxylate functional crosslinkers, isocyanate functional crosslinkers, or combinations thereof. The one or more additional components, one or more additives, or combinations thereof may include any additional components or additives known in the art may be used including, for example, fillers, fibers, surfactants, organic binders, polymeric binders, crosslinking agents, coupling agents, aramid fibers, lubricants, mold release agents, pentaerythritol tetrastearate, nucleating agents, anti-static agents, conductive blacks, carbon fibers, carbon nanotubes, organic antistatic agents, polyalkylene ethers, alkylsulfonates, polyamide-containing polymers, catalysts, colorants, inks, dyes, antioxidants, stabilizers, plasticizers, impact agents, flame retardants, or combinations thereof.

In some embodiments, the method may further include contacting a first epoxy laminant with one or more second epoxy laminants under conditions that allow the first epoxy laminant and the one or more second epoxy laminants to fuse. One or more of the first and the second epoxy laminants may be the optically active epoxy laminant described herein, while any epoxy laminant known in the art may be used as the other epoxy laminant. Any conditions known in the art may be used to achieve fusing of the first epoxy laminant and the one or more second epoxy laminants. Such conditions may include, but are not limited to, stacking the various laminants on top of each other and applying pressure, heat, UV light, or combinations thereof. In some embodiments, the conditions may include applying an adhesive layer on each laminant prior to stacking the various laminants on top of each other.

Further embodiments are directed to methods of identifying a component of a device. Such methods may, generally, include providing a device having a component including an optically active epoxy, and in particular, an optically active epoxy composed of a copolymer of two or more polyepoxides covalently linked by a fused arene, irradiating the device with light, and identifying the component based on its fluorescence. In some embodiments, the device may be irradiated using any UV light source known in the art such as, for example, an arc lamp, a UV light emitting diode (LED), a UV laser, or combinations thereof, and in certain embodiments, the arc lamp, UV LED, or UV laser may be configured to provide a light output through an optic fiber stack. In some embodiments, the UV light source may be configured to be tunable so as to provide light of different wavelengths. Tunable light source may further be configurable with regard to, for example, intensity, wavelength, portability, bandwidth, safety, and the like. In certain embodiments, the UV light may have a wavelength of about 10 nm, about 50 nm, about 100 nm, about 150 nm, about 200 nm, about 250 nm, about 300 nm, about 350 nm, about 400 nm, or any value or range between any two of these values and may result in emission in visible region of the electromagnetic spectrum. For example, the component may have an emission wavelength of about 300 nm, about 320 nm, about 340 nm, about 360 nm, about 380 nm, about 400 nm, about 420 nm, about 440 nm, about 460 nm, about 480 nm, about 500 nm, about 520 nm, about 540 nm, about 560 nm, about 580 nm, about 600 nm, about 620 nm, about 640 nm, about 660 nm, about 680 nm, about 700 nm, or any value or range between any two of these values.

Identifying the component may involve identification of any number of aspects associated with the component based on the fluorescence of the component. For example, in some embodiments, identifying may include determining the specific emission wavelength and correlating the emission wavelength with a type of the component, materials associated with the component, warnings regarding the component, the component manufacturer, manufacture date, the serial number of the component, or the like and combinations thereof. For example, an electrical device may include components that include various optically active epoxies. Certain components may exhibit an emission wavelength of, for example, 500 nm when the component is irradiated with 200 nm wavelength light, which is indicative of a particular manufacturer. The same components may exhibit an emission wavelength of 650 nm when irradiated with 100 nm wavelength light, which may be indicative of a particular part number, date of manufacture, or the like. Other components in the electrical device may emit at different wavelengths when irradiated with the same wavelength excitation light or other components may emit at the same wavelengths when irradiated with different wavelength light providing numerous combinations of excitation and emissions wavelengths that can convey a large amount of information. In certain embodiments, particular excitation and emission wavelengths may be reserved and universally used to convey the type of material used in a particular component. This information may be used to, for example, warn the user or technicians that the materials are hazardous or provide a means for identifying and sorting recyclable materials.

EXAMPLES

Example 1

Optically Active Epoxy with Diphenol Anthracene

Diphenol anthracene is produced via Friedel-Crafts reaction:

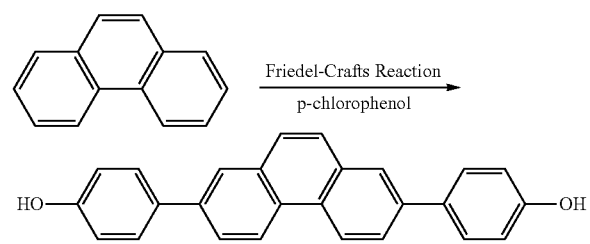

The diphenol anthracene is added to bisphenol-A type epoxy to form a compound of the

Figure 2:
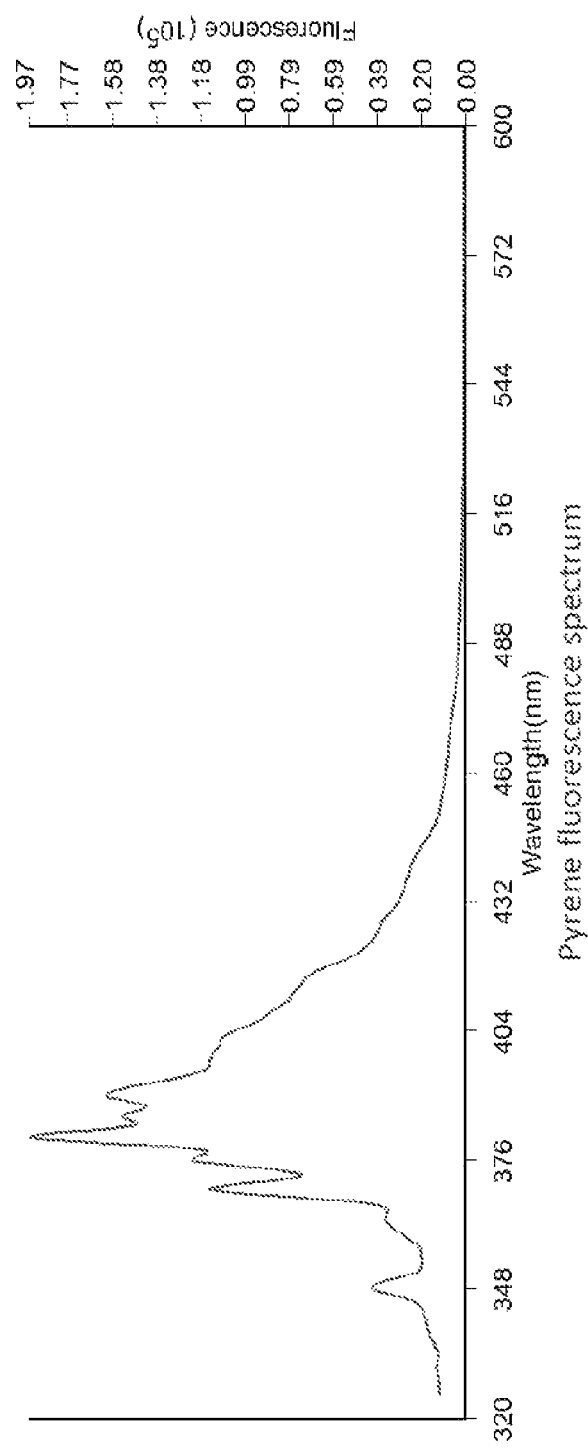
FIG. 2 depicts the fluorescence spectrum of pyrene.

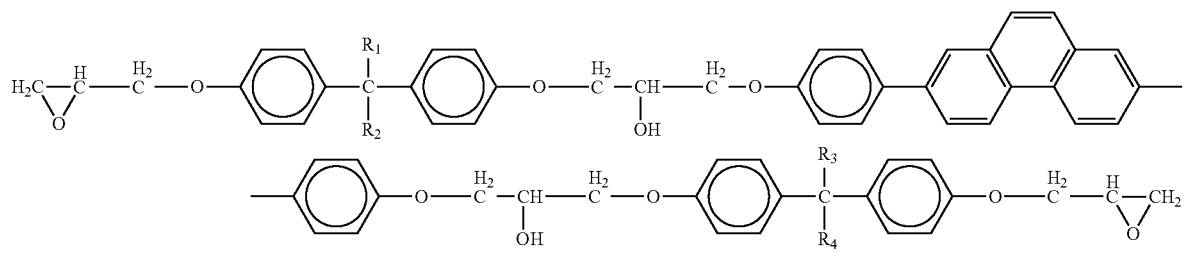

formula:
where m and n can be same or different and any of the $R_1$, $R_2$, $R_3$ and $R_4$ are dependent on the resin of choice. For example, all of $R_1$, $R_2$, $R_3$, and $R_4$ are $CH_3$ (methyl) for a bisphenol-A type epoxy. The fluorescence spectrum for anthracene is shown in FIG. 1, which is modified slightly in view of binding with the phenol groups on both sides.

where m and n can be same or different and any of the $R_1$, $R_2$, $R_3$ and $R_4$ are dependent on the resin of choice. For example, all of $R_1$, $R_2$, $R_3$, and $R_4$ are $CH_3$—(methyl) for a bisphenol-A type epoxy. The fluorescence spectrum for pyrene is shown in FIG. 2, which is modified slightly in view of binding with the phenol groups on both sides.

Example 2

Optically Active Epoxy with Diphenol Pyrene

Diphenol pyrene is produced via Friedel-Crafts reaction:

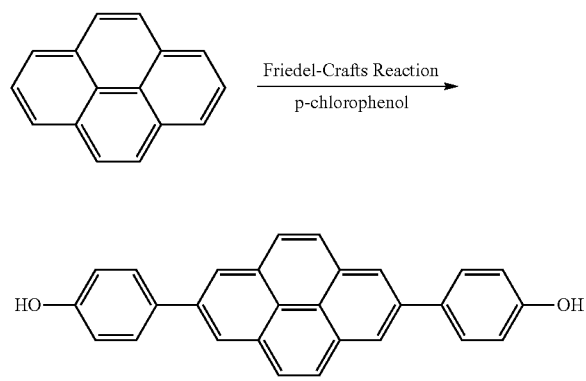

The diphenol pyrene is added to a bisphenol-A type epoxy to form a compound of the formula:

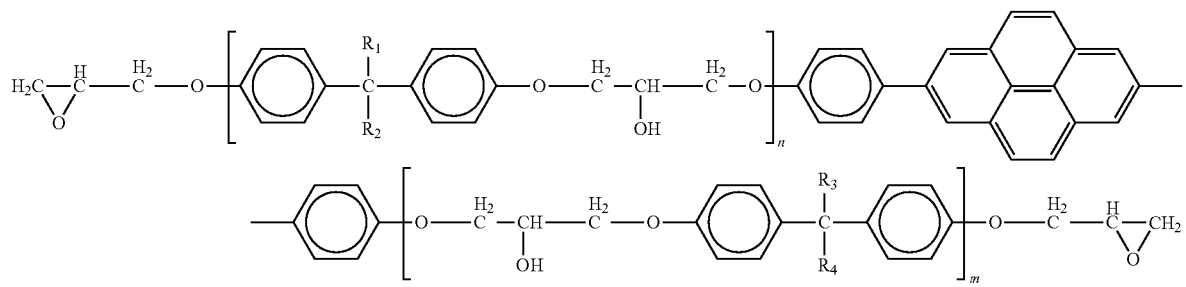

Example 3

Optically Active Epoxy with Diphenol Perylene

Diphenol anthracene is produced via Friedel-Crafts reaction:

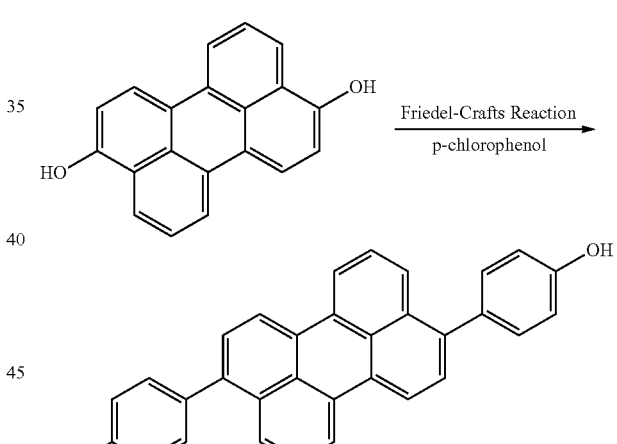

The diphenol perylene is added to bisphenol-A type epoxy to form a compound of the formula:

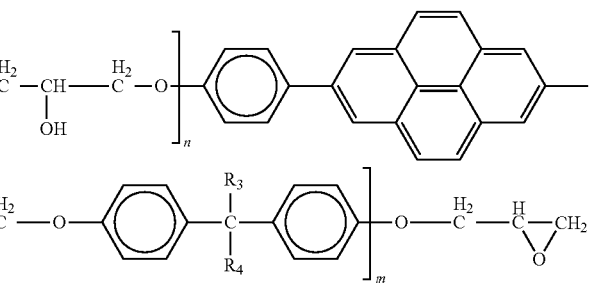

Figure 3:
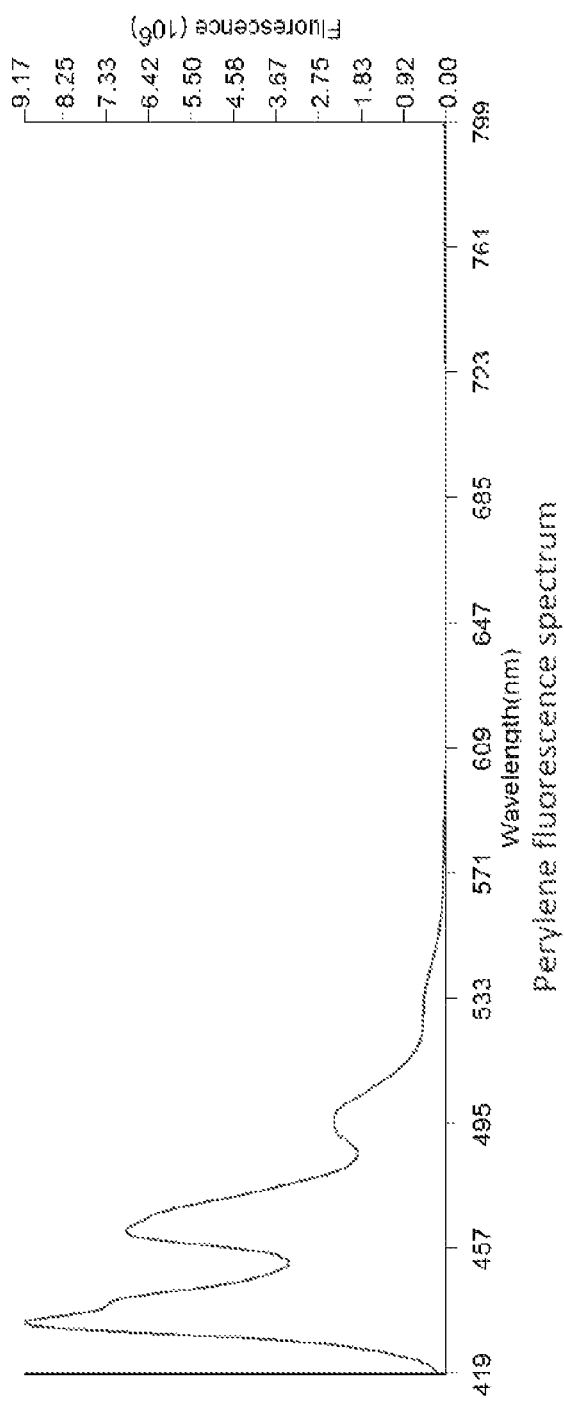
FIG. 3 depicts the fluorescence spectrum of perylene.

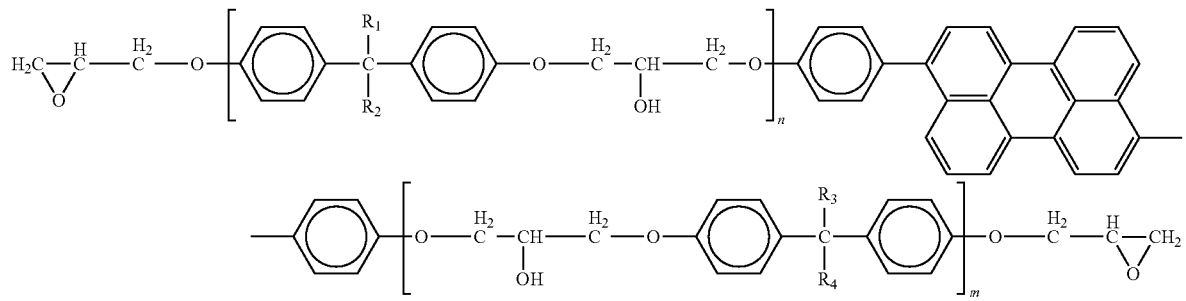

where m and n can be same or different and any of the $R_1$, $R_2$, $R_3$ and $R_4$ are dependent on the resin of choice. For example, all of $R_1$, $R_2$, $R_3$, and $R_4$ are $CH_3$ (methyl) for a bisphenol-A type epoxy. The fluorescence spectrum for perylene is shown in FIG. 3, which is modified slightly in view of binding with the phenol groups on both sides.

Example 4

Optically Active Printed Circuit Boards

About 1%-5% of the optically active epoxy of Example 1 is added to the backbone bisphenol epoxy used for making a printed circuit board to produce printed circuit boards that are optically active and have a fluorescence spectrum similar to that of the epoxy in Example 1.

Example 5

Identification of an Optically Active Printed Circuit Board

A large collection of printed circuit boards, including the printed circuit board of Example 4, is irradiated with ultraviolet (UV) radiation using a UV lamp and the light emitted from the printed circuit board is collected using a UV-visible spectrometer. The specific emission spectrum for the printed circuit board identifies the printed circuit board of Example 4 out of the collection.

Similarly, printed circuit boards containing different optically active epoxies are classified using the specific emission spectra corresponding to the optically epoxies contained therein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A compound comprising a formula:

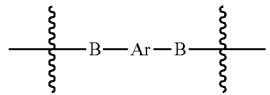

wherein:
B is a polyepoxide; and
Ar is a compound of formula:

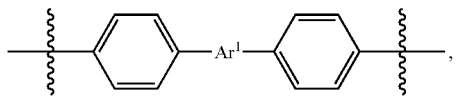

wherein:
$Ar^1$ is a fused arene having 10 to 100 carbon atoms.

2. The compound of claim 1, wherein B comprises bisphenol A epoxy, bisphenol F epoxy, naphthalene epoxy, diphenylfluorene epoxy, triglycidyl aminophenol epoxy, triglycidyl aminocresol epoxy, tetraglycidyl diaminodiphenylmethane epoxy, tetraglycidyl m-xylylene amine epoxy, N,N-diaminocresol epoxy, phenol novolac epoxy, cresol novolac epoxy, biphenyl epoxy, dicyclopentadiene epoxy, or combinations thereof.

3. The compound of claim 1, wherein $Ar^1$ comprises acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, chrysene, dibenz(a,h)anthracene, fluoranthene, fluorene, indeno(1,2,3-cd)pyrene, perylene, phenanthrene, pyrene, or combinations thereof.

4. The compound of claim 1, wherein the compound fluoresces at a wavelength of about 300 nm to about 700 nm when excited by light of wavelength of about 10 nm to about 400 nm.

5. A composition comprising a copolymer of two or more polyepoxides covalently linked by a compound of formula:

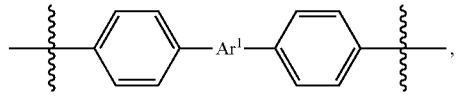

wherein:
$Ar^1$ is fused arene having 10 to 100 carbon atoms.

6. The composition of claim 5, wherein the polyepoxides comprise bisphenol A epoxy, bisphenol F epoxy, naphthalene epoxy, diphenylfluorene-epoxy, triglycidyl aminophenol epoxy, triglycidyl aminocresol epoxy, tetraglycidyl diaminodiphenylmethane epoxy, tetraglycidyl m-xylylene amine epoxy, N,N-diaminocresol epoxy, phenol novolac epoxy, cresol novolac epoxy, biphenyl epoxy, dicyclopentadiene epoxy, and combinations thereof.

7. The composition of claim 5, wherein the fused arene comprises acenaphthene, acenaphthylene, anthracene, benz[a]anthracene, benzo[a]pyrene, benzo[e]pyrene, benzo[b]fluoranthene, benzo[ghi] perylene, benzo[j]fluoranthene, benzo[k]fluoranthene, chrysene, dibenz(a,h)anthracene, fluoranthene, fluorene, indeno(1,2,3-cd)pyrene, perylene, phenanthrene, pyrene, or combinations thereof.

8. The composition of claim 5, wherein the copolymer comprises a formula:

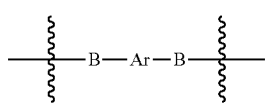

wherein:
B is a polyepoxide; and
Ar is a compound of formula:

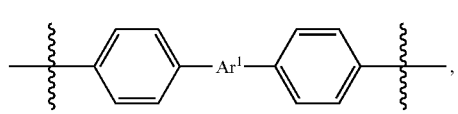

wherein:
$Ar^1$ is fused arene having 10 to 100 carbon atoms.

9. The composition of claim 5, further comprising one or more fillers, fibers, surfactants, organic binders, polymeric binders, crosslinking agents, coupling agents, aramid fibres, lubricants, mold release agents, pentaerythritol tetrastearate, nucleating agents, anti-static agents, conductive blacks, carbon fibers, carbon nanotubes, organic antistatic agents, polyalkylene ethers, alkylsulfonates, polyamide-containing polymers, catalysts, colorants, inks, dyes, antioxidants, stabilizers, plasticizers, impact agents, flame retardants, or combinations thereof.

10. The composition of claim 5, wherein the composition fluoresces at a wavelength of about 300 nm to about 700 nm when excited by light of a wavelength of about 10 nm to about 400 nm.

11. An article of manufacture comprising a copolymer of two or more polyepoxides covalently linked by a compound of formula:

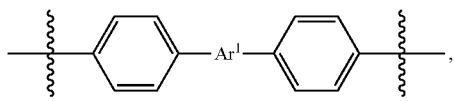

wherein:
$Ar^1$ is a fused arene having 10 to 100 carbon atoms.

12. The article of manufacture of claim 11, wherein the polyepoxides comprise bisphenol A epoxy, bisphenol F epoxy, naphthalene epoxy, diphenylfluorene epoxy, triglycidyl aminophenol epoxy, triglycidyl aminocresol epoxy, tetraglycidyl diaminodiphenylmethane epoxy, tetraglycidyl m-xylylene amine epoxy, N,N-diaminocresol epoxy, phenol novolac epoxy, cresol novolac epoxy, biphenyl epoxy, dicyclopentadiene epoxy, or combinations thereof.

13. The article of manufacture of claim 11, wherein $Ar^1$ comprises acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, chrysene, dibenz(a,h)anthracene, fluoranthene, fluorene, indeno(1,2,3-cd)pyrene, perylene, phenanthrene, pyrene, and combinations thereof.

14. The article of manufacture of claim 11, wherein the copolymer comprises a formula:

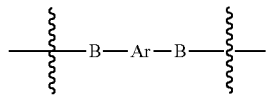

wherein:
B is a polyepoxide; and
Ar is a compound of formula:

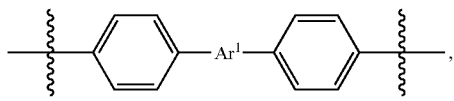

wherein:
$Ar^1$ is fused arene having 10 to 100 carbon atoms.

15. The article of manufacture of claim 11, wherein the article fluoresces at a wavelength of about 300 nm to about 700 nm when excited by light of wavelength 10 nm to 400 nm.

16. The article of manufacture of claim 11, wherein the copolymer comprises a detectable fluorescent tag.

17. A method for preparing an optically active epoxy, the method comprising:
providing at least one functionalized fused arene of formula:

$$X-Ar^2-X'$$

wherein:
$Ar^2$ is a compound of formula:

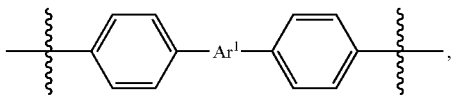

wherein:
$Ar^1$ is a fused arene having 10 to 100 carbon atoms;
X and X' are each independently comprise a functional group; and
contacting the functionalized fused arene with a polyepoxide under conditions that allow the functionalized fused arene to react with the polyepoxide to produce an optically active epoxy.

18. The method of claim 17, further comprising contacting the optically active epoxy with one or more crosslinking agents, one or more curing agents, or combinations thereof under conditions that allow the one or more crosslinking agent, one or more curing agents, or combinations thereof to become incorporated into the optically active epoxy.

19. The method of claim 17, further comprising contacting the optically active epoxy with one or more additional additives under conditions that allow the one or more additional additives to become incorporated into the optically active epoxy.

20. The method of claim 17, wherein $Ar^1$ comprises acenaphthene, acenaphthylene, anthracene, benz[a]anthracene, benzo[a]pyrene, benzo[e]pyrene, benzo[b]fluoranthene, benzo[ghi]perylene, benzo[j]fluoranthene, benzo[k]fluoranthene, chrysene, dibenz(a,h)anthracene, fluoranthene, fluorene, indeno(1,2,3-cd)pyrene, perylene, phenanthrene, pyrene, or combinations thereof.

21. The method of claim 17, wherein X comprises ester, ketone, ether, hydroxyl, carboxylic acid, amine, amino, phenol, aniline, or benzoic acid.

22. The method of claim 17, wherein X' comprises ester, ketone, ether, hydroxyl, carboxylic acid, amine, amino, phenol, aniline, or benzoic acid.

23. The method of claim 17, wherein the optically active epoxy comprises a formula:

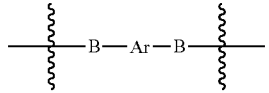

wherein:
B is a polyepoxide; and
Ar is a compound of formula:

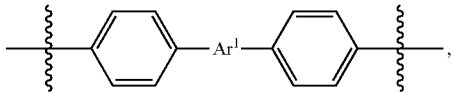

wherein:
$Ar^1$ is fused arene having 10 to 100 carbon atoms.

24. A method for identifying a component of a device, the method comprising:
providing a device having an optically active component including a copolymer of two or more polyepoxides covalently linked by a compound of formula:

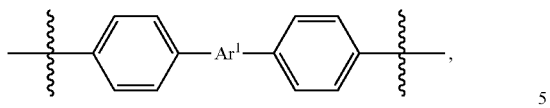

wherein:

Ar$^1$ is a fused arene having 10 to 100 carbon atoms;

irradiating the device with ultraviolet (UV) light having a wavelength of from about 10 to about 400 nm; and identifying the component of the device by determining a fluorescence wavelength emitted by the component, wherein the fluorescence wavelength is from about 300 nm to about 700.

25. The method of claim 24, wherein identifying comprises correlating the fluorescence wavelength with a know fluorescence wavelength corresponding to a property of the component, wherein the property is selected from the group consisting of a type of the component, a material associated with the component, a warning regarding the component, a component manufacturer, a manufacturing date of the component, and a serial number of the component.

* * * * *